United States Patent
Seitz et al.

(10) Patent No.: US 9,108,513 B2
(45) Date of Patent: Aug. 18, 2015

(54) VIEWING DIRECTION AND ACOUSTIC COMMAND BASED OPERATING DEVICE FOR A MOTOR VEHICLE

(75) Inventors: Gordon Seitz, Ehra-Lessien (DE); Moritz Neugebauer, Berlin (DE); Peter Oel, Lehre (DE); Enrique Rodriguez, Mountain View, CA (US); Brian Lathrop, San Jose, CA (US)

(73) Assignee: VOLKSWAGEN AG, Wolfsburg (DE)

( * ) Notice: Subject to any disclaimer, the term of this patent is extended or adjusted under 35 U.S.C. 154(b) by 852 days.

(21) Appl. No.: 12/268,272

(22) Filed: Nov. 10, 2008

(65) Prior Publication Data

US 2010/0121645 A1     May 13, 2010

(51) Int. Cl.
| | | |
|---|---|---|
| *G10L 21/00* | (2013.01) | |
| *G10L 15/00* | (2013.01) | |
| *B60K 35/00* | (2006.01) | |
| *A61B 3/113* | (2006.01) | |
| *B60K 37/06* | (2006.01) | |

(52) U.S. Cl.
CPC .............. *B60K 35/00* (2013.01); *A61B 3/113* (2013.01); *B60K 37/06* (2013.01)

(58) Field of Classification Search
CPC ......... G10L 15/22; G10L 17/22; G10L 15/00; G10L 2015/223; G10L 15/265; G06F 3/167; G06F 3/04842; G06F 3/01; G06F 3/017; G06F 3/048; G06F 3/0482; G06F 3/0488; B60R 16/0373; H04N 2005/4428
USPC ...................... 704/270, 270.1, 275, 231, 246; 707/104.1; 715/728, 831
See application file for complete search history.

(56) References Cited

U.S. PATENT DOCUMENTS

| | | | | |
|---|---|---|---|---|
| 5,368,484 | A | * | 11/1994 | Copperman et al. ............. 434/69 |
| 5,607,308 | A | * | 3/1997 | Copperman et al. ............. 434/62 |
| 5,618,178 | A | * | 4/1997 | Copperman et al. ............. 434/62 |
| 5,689,619 | A | | 11/1997 | Smyth |
| 6,010,403 | A | * | 1/2000 | Adam et al. ....................... 463/6 |
| 6,157,403 | A | * | 12/2000 | Nagata ........................... 348/171 |
| 6,675,075 | B1 | | 1/2004 | Engelsberg et al. |
| 6,853,972 | B2 | | 2/2005 | Friedrich et al. |

(Continued)

FOREIGN PATENT DOCUMENTS

| | | |
|---|---|---|
| DE | 199 51 001 | 5/2001 |
| DE | 695 24 829 | 6/2002 |

(Continued)

OTHER PUBLICATIONS

Alice Oh, Harold Fox, Max Van Kleek, Aaron Adler, Krzystof Gajos, Louis-Philippe Morency, Trevor Darrell, "Evaluating Look-To-Talk: A Gaze-Aware interface In A Collaborative Environment", Proceedings of CHI 2002.*
Qiahui Zhang; Go, K.; Imamiya, A.; Xiaoyang Mao;, "Designing a robust speech and gaze multimodal system for diverse users," Information Reuse and Integration, 2003. IRI 2003. IEEE International Conference on , vol., no., pp. 354-361, Oct. 27-29, 2003.*
www.tobii.com/archive/files/17992/Tobii_X120_Eye_Tracker_product_leaflet.pdf.aspx., [retrieved from internet Aug. 3, 2009].
www.tobii.com/market_research_usability/products_services/tobii_x120_eye_trackcr.aspx . . . ; copyright 2008. [retrieved from internet Aug. 3, 2009].

*Primary Examiner* — Edgar Guerra-Erazo
(74) *Attorney, Agent, or Firm* — Kenyon & Kenyon LLP

(57) ABSTRACT

In a method for the operator control of a motor vehicle having a display for displaying variable information and having a microphone, the viewing direction of an operator of the motor vehicle is ascertained, it is checked whether the viewing direction of the operator is aimed toward the display, and information assigned to an acoustic command is shown on the display when a corresponding acoustic command is given while the viewing direction of the operator is aimed toward the display.

13 Claims, 6 Drawing Sheets

(56) References Cited

U.S. PATENT DOCUMENTS

| | | | |
|---|---|---|---|
| 7,924,506 B2 * | 4/2011 | Rieger | 359/630 |
| 2004/0097195 A1 * | 5/2004 | Selleck | 455/41.3 |
| 2005/0175218 A1 * | 8/2005 | Vertegaal et al. | 382/103 |
| 2006/0110008 A1 * | 5/2006 | Vertegaal et al. | 382/103 |
| 2007/0016426 A1 * | 1/2007 | Hershey et al. | 704/277 |
| 2007/0024579 A1 | 2/2007 | Rosenberg | |
| 2007/0040892 A1 * | 2/2007 | Aoki et al. | 348/14.01 |
| 2007/0057781 A1 | 3/2007 | Breed | |
| 2007/0081090 A1 * | 4/2007 | Singh | 348/333.11 |
| 2007/0194902 A1 | 8/2007 | Blanco et al. | |
| 2007/0233380 A1 | 10/2007 | Tanaka | |
| 2007/0256027 A1 | 11/2007 | Daude | |
| 2008/0021598 A1 | 1/2008 | Daude et al. | |
| 2008/0201039 A1 | 8/2008 | Matsuoka et al. | |
| 2008/0278821 A1 * | 11/2008 | Rieger | 359/630 |
| 2009/0125233 A1 | 5/2009 | Shibasaki | |

FOREIGN PATENT DOCUMENTS

| | | |
|---|---|---|
| DE | 103 60 655 | 7/2005 |
| DE | 103 60 656 | 7/2005 |
| DE | 10 2005 023 214 | 11/2006 |
| EP | 0 702 355 | 3/1996 |
| JP | 11-263145 | 9/1999 |
| WO | WO 98/15964 | 4/1998 |

* cited by examiner

VIEWING DIRECTION AND ACOUSTIC COMMAND BASED OPERATING DEVICE FOR A MOTOR VEHICLE

FIELD OF THE INVENTION

The present invention relates to an operating device for a motor vehicle, e.g., having a display for displaying variable information, an eye tracker for ascertaining the viewing direction of an operator of the motor vehicle and a microphone for the acoustic input of commands.

BACKGROUND INFORMATION

German Published Patent Application No. 199 51 001 describes a device for displaying information in a vehicle, the device having various devices for the display; the various devices for the display displaying the information; various data sources making the information available; the device having various devices for detecting the viewing direction of a driver of the vehicle; the devices for detecting the viewing direction detecting the viewing direction of the driver; the device having a computer; the computer being connected to the devices for detecting the viewing direction and to the various devices for the display; the computer obtaining the viewing direction of the driver of the vehicle from the devices for detecting the viewing direction; and the computer passing on the viewing direction of the driver of the vehicle to the various devices for the display so that the various devices for the display therefore show the information as a function of the viewing direction of the driver of the vehicle.

U.S. Patent Application Publication No. 2007/0057781 describes what is referred to as a head-up display, integrated into a motor vehicle, that interacts with a voice-recognition system and/or gesture-recognition system. Further operating devices for motor vehicles are described, for example, in Japanese Published Patent Application No. 11-263145, German Published Patent Application No. 103 60 655, German Published Patent Application No. 10 2005 023 214, German Published Patent Application No. 103 60 656, and PCT International Published Patent Application No. WO 98/15964.

European Published Patent Application No. 0 702 355 and German Published Patent Application No. 695 24 829 describe a voice-recognition device for recognizing input speech, that includes a detector for detecting the point toward which the eyes of a user are focused on a display screen, as well as a modification device for modifying recognition processing for a voice recognition in accordance with the point detected by the detector. Moreover, the voice-recognition device includes a recognition device for performing the voice recognition in accordance with the recognition processing modified by the modification device. In this context, the modification device is configured, in particular, to modify classes of recognition information, which are to be used for the voice recognition, in accordance with the point detected by the detector, and to set a plurality of fields, each of which is specific to a different class of recognition information.

SUMMARY

Example embodiments of the present invention improve the operator control of a motor vehicle. In so doing, the improvement is to be aimed, in particular, at permitting a precise and rapid operator control of the motor vehicle, the driver being distracted as briefly as possible or not at all from what is happening on the road. Moreover, an aspect hereof is to take into consideration the special circumstances with regard to a particular background noise in the vehicle interior, particularly at high speeds.

Example embodiments of the present invention provide a method for the operator control of a motor vehicle having a display for displaying variable information and having a microphone, the method including: ascertaining the viewing direction of an operator of the motor vehicle; checking whether the viewing direction of the operator is turned toward the display; and evaluating an output signal of the microphone for the purpose of recognizing acoustic commands; showing information assigned to an acoustic command on the display when the acoustic command is given while the viewing direction of the operator is aimed toward the display.

Information assigned to an acoustic command may include, in particular, information with regard to a function pertaining to a motor vehicle. For example, a function pertaining to a motor vehicle may be an air conditioner or automatic climate control, a navigation system, a telephone, a window lift, etc., or a screen form, displayable by a display device, for operating an air conditioner or automatic climate control, a screen form, displayable by a display device, for operating a navigation system, a screen form, displayable by a display device, for operating a telephone, etc. Further examples for functions pertaining to the motor vehicle along these lines are described below.

Information assigned to an acoustic command may include, in particular, information having a pure display content or a screen form for assistance in the control of a function of the motor vehicle.

The input of an acoustic command while the direction of view is pointed toward the display may be understood particularly narrowly, that is, only an acoustic command is accepted which has occurred while at the same time the direction of view is aimed toward the display. However, the input of an acoustic command while the direction of view is pointed toward the display may also be understood such that a close temporal relationship exists between the acoustic command and the pointing of the direction of view toward the display. In this context, in particular, it is provided that the eye is initially directed toward the display, and during or shortly after this state, the corresponding acoustic command is given. Shortly thereafter in this sense is intended especially to be understood as a time span of no more than, e.g., 2 seconds.

The information assigned to the acoustic command may be shown on a display of an instrument cluster. The information assigned to the acoustic command may be shown on a display arranged next to the steering wheel of the motor vehicle. The information assigned to the acoustic command may be shown on a head-up display. The information assigned to the acoustic command may be shown on the display only if the eye of the operator of the motor vehicle is directed toward the symbol longer than a predefined limiting value.

In addition, example embodiments of the present invention provide an operating device for a motor vehicle including: a display for displaying variable information; an eye tracker for ascertaining the viewing direction of an operator of the motor vehicle; a microphone for the acoustic input of commands; and a control for showing information assigned to an acoustic command on the display when the acoustic command is given while the viewing direction of the operator is aimed toward the display.

Exemplary eye trackers are described, for example, from the following Internet pages:
www.tobii.com/archive/files/17992/
Tobii_X120_Eye_Tracker_product_leaflet.pdf.aspx
www.tobii.com/market_research_usability/products_services/tobii_x120_eye_tracker.aspx The display may be integrated into an instrument cluster. The display may be positioned next to a steering wheel of the motor vehicle. The display may be in the form of a head-up display.

In addition, example embodiments of the present invention provide an operating device for a motor vehicle including: a display system, the display system including at least two displays from the following group: display integrated into an instrument cluster for displaying variable information, display positioned next to the steering wheel of the motor vehicle for displaying variable information, and head-up display for displaying variable information; an eye tracker for ascertaining the viewing direction of an operator of the motor vehicle; a microphone for the acoustic input of commands; and a control for showing information assigned to an acoustic command on that display toward which the viewing direction of the operator is aimed while the acoustic command is given.

Example embodiments of the present invention provide an operating device for a motor vehicle including: a display system, the display system including a display integrated into an instrument cluster for displaying variable information, a display positioned next to the steering wheel of the motor vehicle for displaying variable information, and a head-up display for displaying variable information; an eye tracker for ascertaining the viewing direction of an operator of the motor vehicle; a microphone for the acoustic input of commands; and a control for showing information assigned to an acoustic command on that display toward which the viewing direction of the operator is aimed while the acoustic command is given.

A motor vehicle may be, e.g., a land vehicle that may be used individually in road traffic. In particular, motor vehicles are not restricted to land vehicles having an internal combustion engine.

Further features and aspects of example embodiments of the present invention are described in more detail below with reference to the appended Figures.

DETAILED DESCRIPTION

Figure 1:
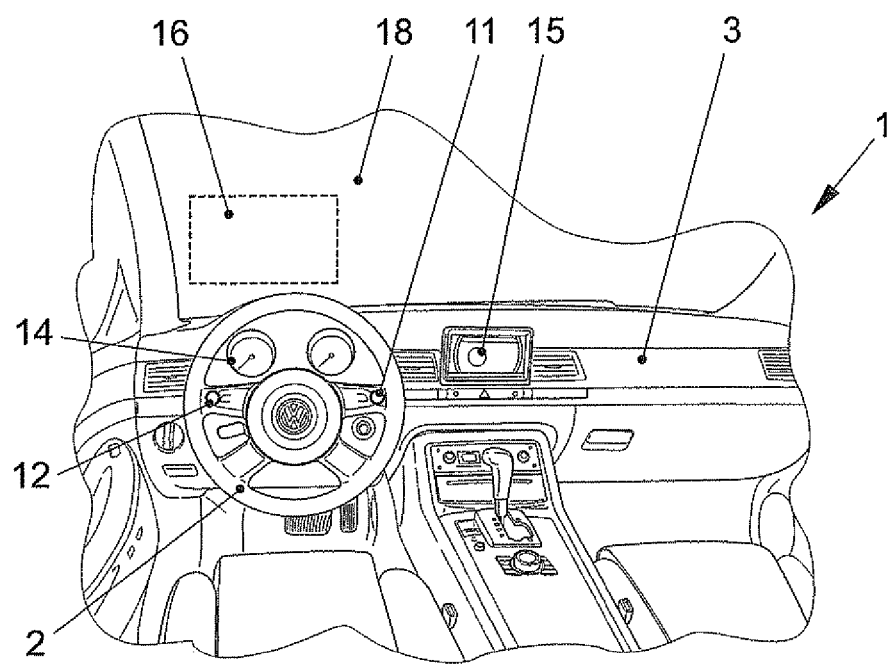
FIG. 1 illustrates an exemplary embodiment of an interior view of a motor vehicle.
Figure 2:
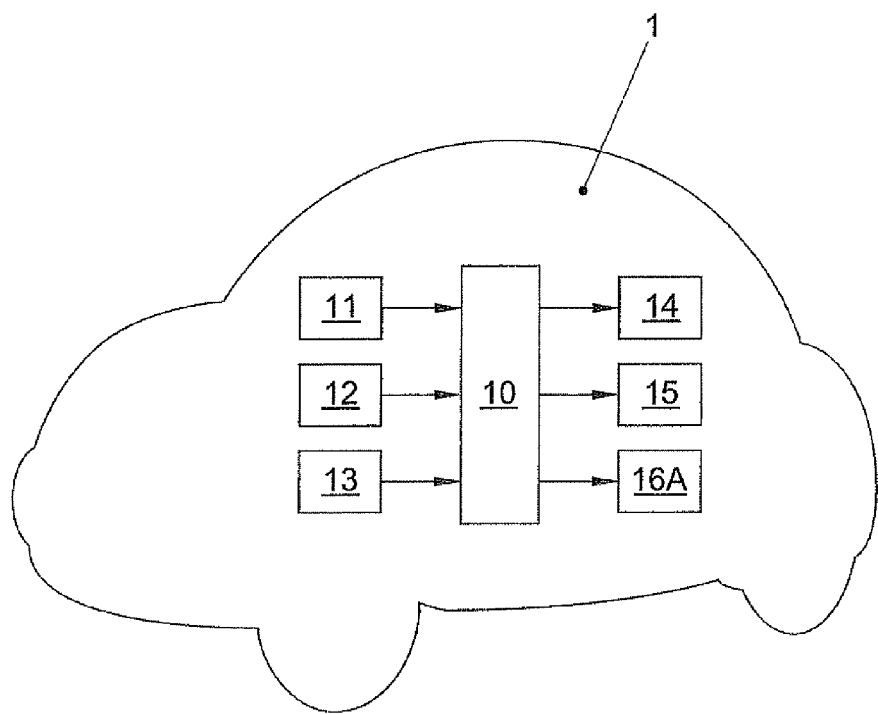
FIG. 2 schematically illustrates an exemplary embodiment of a motor vehicle having an operating device.

FIG. 1 shows the interior view of a motor vehicle 1, which is schematically illustrated in FIG. 2. Motor vehicle 1 includes an operating device having a microphone 11, disposed on steering wheel 2 of motor vehicle 1 in the exemplary embodiment, for the input of acoustic commands (e.g., for the input of voice commands), and having a display 15, located on dashboard 3 of motor vehicle 1, for displaying variable information. In addition, the operating device includes an eye tracker 13, a heads-up display as well as an instrument cluster 14, situated in front of steering wheel 2, that includes a display for showing variable information. The heads-up display includes a projection device 16A for projecting information in a display area 16 on windshield 18 of motor vehicle 1. Moreover, the operating device includes a control 10 for controlling the display of instrument cluster 14, the heads-up display, i.e., projection device 16A, as well as display 15.

Figure 3:
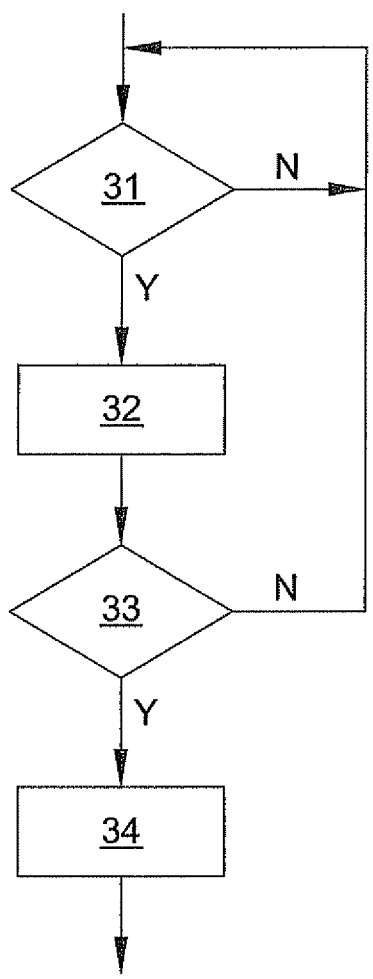
FIG. 3 schematically illustrates a method sequence.

FIG. 3 schematically illustrates a flowchart of a method, implemented in control 10, for the operator control of motor vehicle 1. In this context, with the aid of an (optional) query 31, it is checked whether an operating element 12 (see FIG. 2) for activating an eye tracker has been manipulated. If such a manipulation has taken place, then following query 31, in 32, a viewing direction is detected with the aid of eye tracker 13 (see FIG. 2). On the other hand, if no such manipulation has taken place, then query 31 is repeated, possibly only a certain number of repetitions being allowed.

Detection, in 32, is followed by a query 33 as to whether the eye tracking in 32 reveals that the direction of view or the eye of the driver of motor vehicle 1 is directed toward instrument cluster 14, display 15 or projection area 16, and whether, with the aid of microphone 11, an acoustic command to display available information has been received.

If the direction of view or the eye of the driver of motor vehicle 1 is directed toward instrument cluster 14, display 15 or projection area 16, and with the aid of microphone 11, an acoustic command to display available information has been received, then query 33 is followed by 34. Otherwise, query 33 is followed by query 31. In 34, the information assigned to the acoustic command is shown on the display toward which the direction of view or the eye of the driver was directed while the acoustic command took place.

Figure 4:
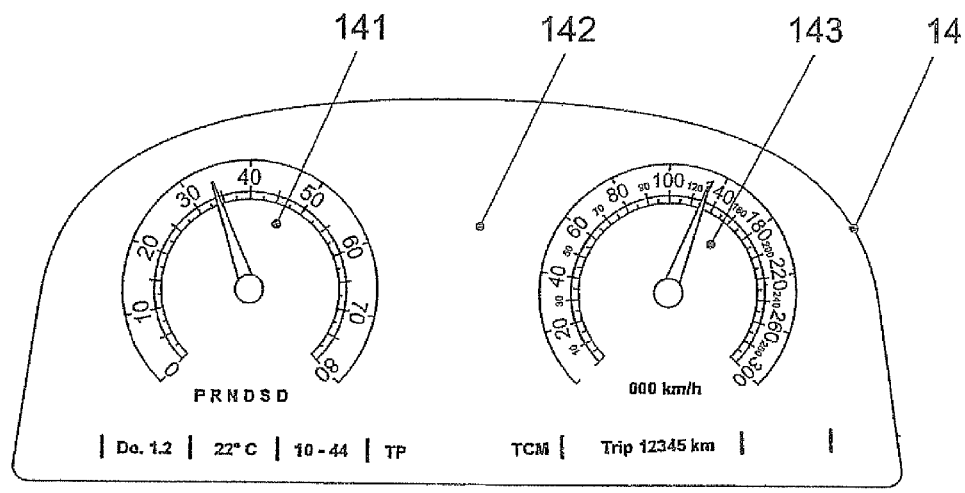
FIG. 4 illustrates an exemplary embodiment of an instrument cluster.
Figure 5:
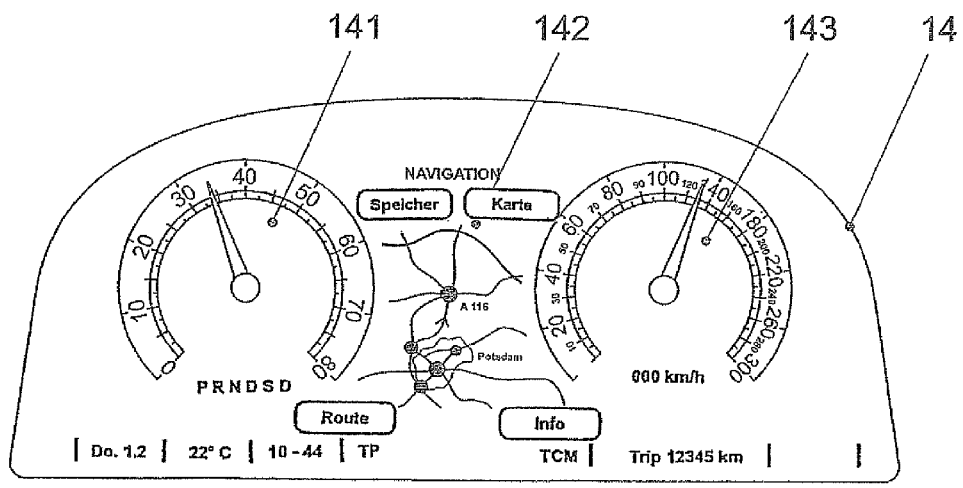
FIG. 5 illustrates the instrument cluster illustrated in FIG. 4 in a state in which functions of a navigation system are displayed.

For example, if the eye or the viewing direction of the driver of motor vehicle 1 is directed toward instrument cluster 14, and the acoustic command is "navi" or "navigation system," then—as explained with reference to FIGS. 4 and 5—a screen form for operating a navigation system is displayed. In FIGS. 4 and 5, reference numeral 141 denotes an analog display for indicating the engine speed of motor vehicle 1, and reference numeral 143 denotes an analog display for indicating the velocity of motor vehicle 1. Reference numeral 142 denotes a display for showing variable information. As depicted, for example, in FIG. 5, the screen form for operating a navigation system is shown on display 142 when the acoustic command "navi" or "navigation system" is given while the eye or the direction of view of the driver of motor vehicle 1 is aimed toward instrument cluster 14.

Figure 6:
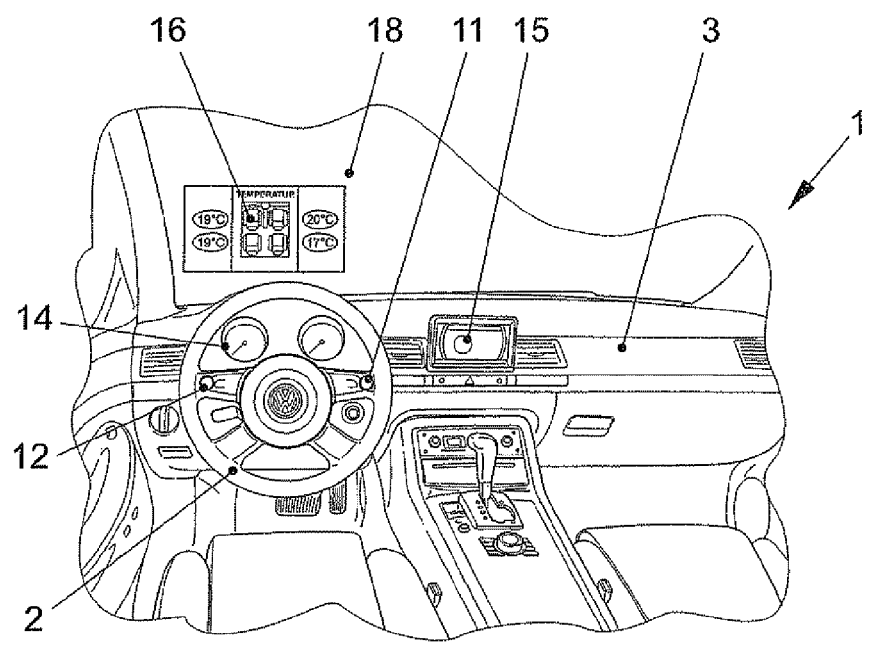
FIG. 6 illustrates the interior view of the motor vehicle illustrated in FIG. 1 having an indicator with the aid of a heads-up display.

If the eye or the viewing direction of the driver of motor vehicle 1 is turned toward projection area 16 and the acoustic command "warmer," "colder," "climate," "air-conditioner," "automatic climate control," or "aircon" is given, then with the aid of projection device 16A, a status indication of the automatic climate control or a screen form for operating the automatic climate control of motor vehicle 1 is displayed in projection area 16, as shown, for example, in FIG. 6.

Figure 7:
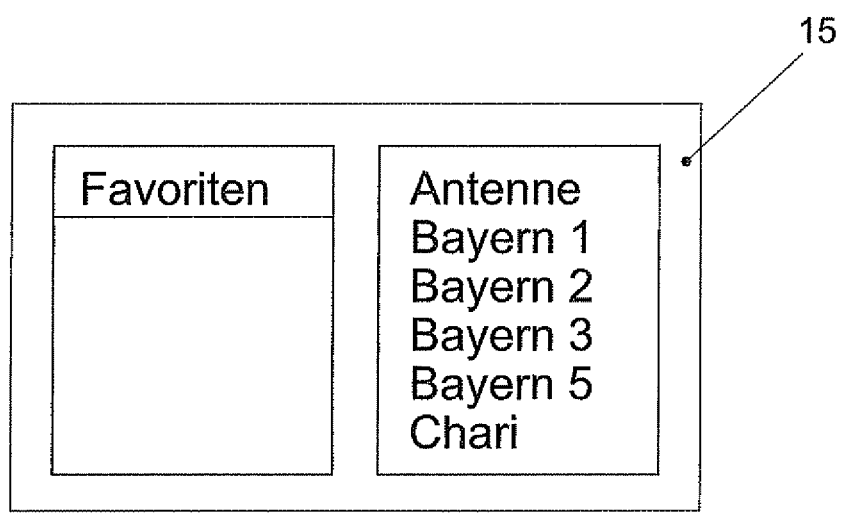
FIG. 7 illustrates an exemplary embodiment of a display.

If the eye or the viewing direction of the driver of motor vehicle 1 is turned toward display is and the acoustic command "radio" is given, then—as shown, for example, in FIG. 7—a screen form for operating a radio is shown with the aid of display 15. On the other hand, if the eye or the direction of view of the driver of motor vehicle 1 is aimed toward instrument cluster 14, i.e., toward display 142 and the acoustic command "radio" is given, then the screen form for operating a radio is shown with the aid of display 142.

LIST OF REFERENCE NUMERALS

1 motor vehicle
2 steering wheel
3 dashboard
10 control
11 microphone
12 operating element for activating an eye tracker
13 eye tracker
14, 142 instrument cluster
15 display
16 display area
16A projection device
18 windshield
31, 33 query
32, 34 step
141 analog display for indicating a speed of an engine of a motor vehicle
143 analog display for indicating the velocity of a motor vehicle

What is claimed is:

1. A method for operator control of a motor vehicle having a plurality of displays for displaying variable information and having a microphone, comprising:
    ascertaining a viewing direction of an operator of the motor vehicle;
    determining whether the viewing direction of the operator is aimed toward one of the plurality of displays;
    identifying toward which of the plurality of displays the viewing direction of the operator is aimed;
    evaluating an output signal of the microphone to recognize acoustic commands;
    choosing one of the plurality of displays for displaying information based on the viewing direction of the operator when an acoustic command is given; and
    displaying information assigned to the acoustic command on the chosen display.

2. The method according to claim 1, wherein the displaying includes displaying the information assigned to the acoustic command on a display of an instrument cluster.

3. The method according to claim 1, wherein the displaying includes displaying information assigned to the acoustic command on a display arranged next to a steering wheel of the motor vehicle.

4. The method according to claim 1, wherein the displaying includes displaying information assigned to the acoustic command on a heads-up display.

5. The method according to claim 1, wherein the displaying includes displaying information assigned to the acoustic command on the display only if an eye of the operator of the motor vehicle is directed toward a symbol longer than a predefined limiting value.

6. An operating device for a motor vehicle, comprising:
    a plurality of displays configured to display variable information;
    an eye tracker configured to ascertain a viewing direction of an operator of the motor vehicle;
    a microphone configured to receive an acoustic input of commands; and
    a control configured to choose one of the plurality of displays to display information based on the viewing direction of the operator when an acoustic command is given, and configured to display information assigned to the acoustic command on the chosen display.

7. The operating device according to claim 6, wherein the display is integrated into an instrument cluster.

8. The operating device according to claim 6, wherein the display is positioned next to a steering wheel of the motor vehicle.

9. The operating device according to claim 6, wherein the display includes a heads-up display.

10. An operating device for a motor vehicle, comprising:
    a display system including at least two of the following displays: (a) a display integrated into an instrument cluster configured to display variable information; (b) a display positioned next to a steering wheel of the motor vehicle configured to display variable information; and (c) a heads-up display configured to display variable information;
    an eye tracker configured to ascertain a viewing direction of an operator of the motor vehicle;
    a microphone configured to receive an acoustic input of commands; and
    a control configured to choose one of the displays of the display system to display information based on the viewing direction of the operator when an acoustic command is given, and configured to display information assigned to the acoustic command on the chosen display.

11. An operating device for a motor vehicle, comprising:
    a display system including a display integrated into an instrument cluster configured to display variable information, a display positioned next to a steering wheel of the motor vehicle configured to display variable information, and a heads-up display configured to display variable information;
    an eye tracker configured to ascertain a viewing direction of an operator of the motor vehicle;
    a microphone configured to receive an acoustic input of commands; and
    a control configured to choose one of the displays of the display system to display information based on the viewing direction of the operator when an acoustic command is given, and configured to display information assigned to the acoustic command on the chosen display.

12. The method according to claim 1, wherein the acoustic command is recognized independently of the viewing direction.

13. The method according to claim 1, wherein the acoustic command is recognized independently of any information displayed on the display prior to giving the acoustic command.

* * * * *